United States Patent [19]

Wiedner

[11] Patent Number: 4,835,796
[45] Date of Patent: Jun. 6, 1989

[54] GOGGLES FOR PROTECTION AGAINST LASER RADIATION

[75] Inventor: Klaus Wiedner, Furth/Bay, Fed. Rep. of Germany

[73] Assignee: UVEX Winter Optik GmbH, Fuerth/Bay, Fed. Rep. of Germany

[21] Appl. No.: 104,114

[22] Filed: Oct. 1, 1987

[51] Int. Cl.[4] ............................................. A61F 9/02
[52] U.S. Cl. ............................................. 2/431; 351/44
[58] Field of Search .............. 2/426, 431, 432, 433, 2/449, 51, 2; 351/48, 47, 44; 423/448

[56] References Cited

U.S. PATENT DOCUMENTS

| | | | |
|---|---|---|---|
| 3,519,339 | 7/1970 | Hutchinson et al. | 351/44 |
| 4,400,433 | 8/1983 | Ishiguro et al. | 423/448 |
| 4,511,225 | 4/1985 | Lipson | 2/432 |
| 4,533,086 | 8/1985 | Junttila | 423/448 |
| 4,611,588 | 9/1986 | Laptewicz, Jr. et al. | 128/132 R |
| 4,650,287 | 3/1987 | Kudo et al. | 350/322 |
| 4,703,522 | 11/1987 | Schürle et al. | 2/432 |

FOREIGN PATENT DOCUMENTS 8532493 11/1985 Fed. Rep. of Germany .

Primary Examiner—Werner H. Schroeder
Assistant Examiner—Jeanette E. Chapman
Attorney, Agent, or Firm—Browdy and Neimark

[57] ABSTRACT

Protective goggles against laser radiation comprises a frame, particularly of plastic and containing protective lenses, its inside being at least partially covered with a shielding layer made from another material for attaining a large degree of protection, the shielding layer being formed of a flexible graphite material.

3 Claims, 1 Drawing Sheet

GOGGLES FOR PROTECTION AGAINST LASER RADIATION

FIELD OF THE INVENTION

The invention relates to goggles for protection against laser radiation, comprising a frame, particularly made of plastic and containing the protective lenses, the inside of which is at least partially covered with a shielding of another material.

BACKGROUND OF THE INVENTION

Such goggles useful for protection against laser radiation are known, for example, from German Utility Patent DE-GM 85 32 493. Stamped sheet metal parts, primarily of sheet metal having good heat conduction properties, are used with these known goggles.

By providing such shielding, a dependable protection for the eyes of the user independently of the particular angle at which the head is bent, is warranted even when the laser beam does not penetrate through the protective lenses but impinges on the goggle frame from the side, for example.

A significant disadvantage of the known goggles lies in the fact that when using sheet metal parts of sufficient thickness to achieve a satisfactory protective result, the weight of the goggles is considerably increased. This is considered a grave problem, especially in connection with sensitive work such as, for example, during the use of a laser by a physician during surgery. Additionally, stamped sheet metal parts must be either carefully finished or additional protection or padding must be provided to avoid injury to the face of the user or an unpleasant feeling of pressure caused by sheet metal parts which may touch the face. Finally, the making and shaping of suitable sheet metal parts as well as their combination with the frame result in a not inconsiderable amount of expense in their manufacture.

SUMMARY OF THE INVENTION

Based on these considerations it is an object of the present invention to improve goggles for protection against laser radiation of the type mentioned above in such a way that they provide great ease of wear and, at the same time, good protective results and cost-efficient manufacture.

This object is attained by means of the invention through the use of flexible graphite material as shielding. Such graphite material has good heat conductive properties comparable to those of metals, thus avoiding local overheating which might lead to damage when a laser beam, especially a $CO_2$-laser impinges on it. Furthermore, such a material can be easily worked because it can be stamped into the shape desired and then bent into the shape desired without the need of machinery.

It is especially advantageous to form the flexible graphite material in layer form by means of pressed flakes of pure graphite. Such a layer has foil-like properties. i.e. it can be handled and shaped like a foil. Besides this property which is advantageous for manufacture, it is of considerable importance that such a layer has a very high anisotropy of its heat conductivity vertically as compared to heat conductivity parallel to the plane of the layer. The heat conductivity parallel to the plane of the layer is very great; in contrast thereto, its heat conductivity vertically (i.e. across the plane) is, for example, twenty-seven times less. In connection with the use according to the invention this means that a very good and rapid heat dissipation in the plane of the layer takes place upon impingement of a laser beam, but that in contrast thereto vertically to the plane of the layer, i.e. in the direction of the beam and thus in the direction of the eyes of the user, heat conductivity is very poor, thus resulting in a dependable protective function.

It is advantageous to extend the shielding across the side parts of the goggle frame and the area of the bridge of the nose. The main imperiled areas are thus covered.

It is of particular advantage to form the shielding by a one-piece cutting. The formation of unshielded areas at the places were individual cuts meet is thus prevented and, at the same time, manufacture and mounting is simplified.

The most advantageous way of mounting the pre-stamped shielding is by gluing it into the goggle frame. Such gluing by means of customary adhesives is easily possible in connection with the graphite layers considered.

The invention is also directed to the use of a layer formed by a graphite material of pressed flakes of pure graphite as a shielding against laser radiation. In addition to the goggle previously described, face shields or body shields as well as protective clothing of all types can be equipped with such shielding while maintaining the advantages obtained by the previously described anisotropic heat distribution. Such a shielding layer can also be covered with aluminum foil.

Further characteristics, advantages and details of the invention are contained in the following description of a preferred embodiment by means of the drawings.

DETAILED DESCRIPTION OF THE PREFERRED EMBODIMENT

Figure 1:
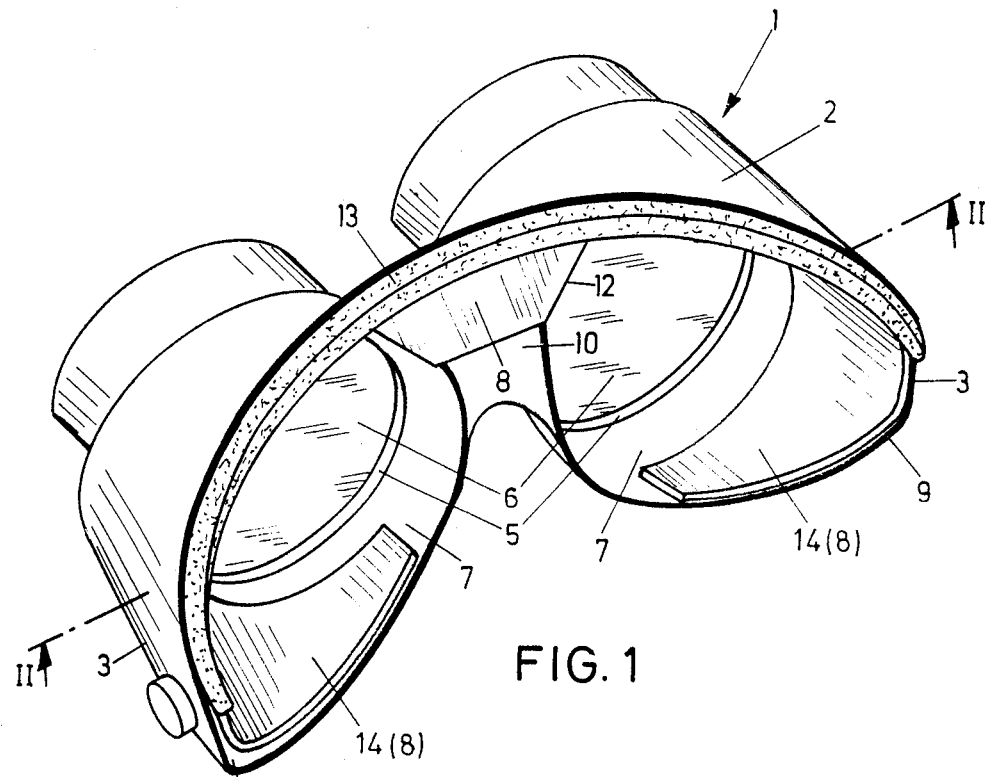
FIG. 1 is a perspective view of the inside of the protective goggles against laser radiation according to the invention, the bows or temples being excluded for reasons of clarity.
Figure 2:
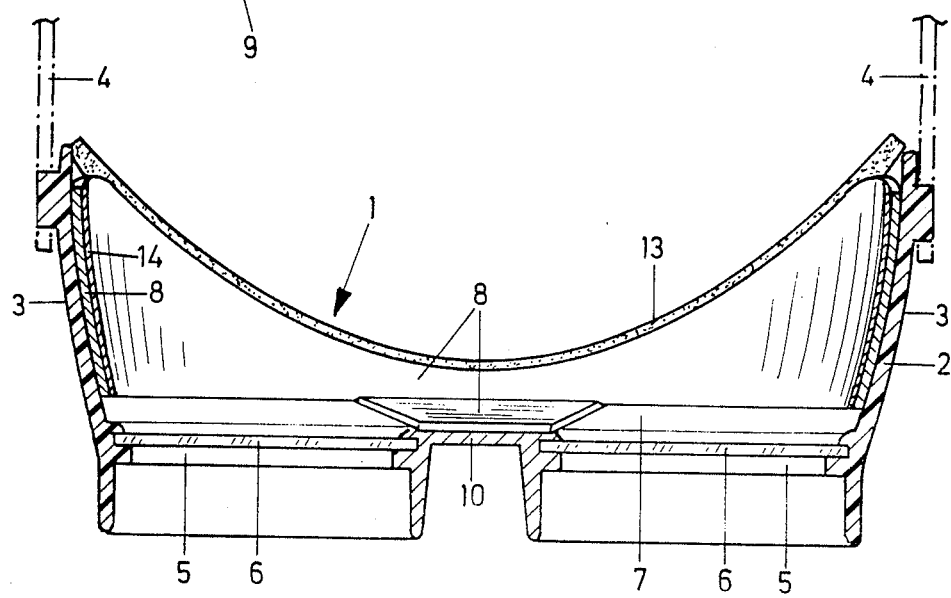
FIG. 2 is a section along line II—II through the frame parallel to the plane of the lenses.

Goggles 1 shown in the drawing have a frame 2 made of plastic, on the side shields 3 of which bows or temples 4, not shown in detail, have been disposed. The frame 2, having a closed box-like form, has two recesses 5 into which special laser protection lenses 6 are inserted.

A layer 8 of graphite, more particularly of pressed flakes of pure graphite, is attached by gluing to the inner wall 7 of the frame 2 which is molded in one piece. The graphite layer 8 is been made from a single cutting and, in the attached state, extends along the inside of the side shields 3 via the lower frame parts 9 placed in front of the lenses 6 in one piece across the nose area 10, the area of the bridge of the nose being covered by a bent projection 12. A padding strip 13 of foam material extends along the upper edge of the frame 2.

The graphite shielding employed has a very good temperature resistance or, better stated, temperature change resistance; has a soft surface; and can be easily worked by cutting or stamping and glued with adhesive available in the trade. Of special importance for the protective use desired in connection with the invention is particularly the anisotropic coefficient of approximately 27 for heat conductivity parallel to the plane of the layer as compared with its conductivity vertically through the layer.

To the extent that a frame or, respectively, protective lenses are mentioned in the course of this application, this is to be understood in the general sense of these words, i.e. the invention particularly also includes so-called full vision goggles having a housing-like plastic frame and a single lens extending across it.

The graphite shielding preferably used is commercially available under the trade name "SIGRAFLEX".

The flexible graphite shielding layer is covered with an aluminum foil 14.

It is to be understood that the above description of an exemplary embodiment is by way of example only and that further improvements and variants are possible within the scope of the invention.

What is claimed is:

1. Protective goggles against laser radiation comprising:
   a frame including side shields and containing at least one protective lens;
   wherein said goggles comprise a light weight frame, having a generally box-like configuration and said shielding extends across the side shields and the area of the bridge of the nose;
   wherein the inside of said frame is at least partially covered with a layer of a flexible graphite shielding material;
   wherein said flexible graphite shielding material is formed of pressed flakes of pure graphite;
   wherein said flexible graphite shielding layer is covered with aluminum foil; and
   wherein the shielding is glued to the inside of the goggle frame.

2. Protective goggles against laser radiation in accordance with claim 1, wherein said shielding is in the form of a one-piece cutting.

3. Protective goggles according to claim 1 wherein said light weight frame is plastic.

* * * * *